United States Patent
Davé et al.

(10) Patent No.: US 6,538,104 B2
(45) Date of Patent: Mar. 25, 2003

(54) STABILIZATION OF CARDIAC TROPONIN I SUBUNITS AND COMPLEXES

(75) Inventors: Kirti I. Davé, Thousand Oaks, CA (US); Brian Robert Fernández, Tarzana, CA (US)

(73) Assignee: Medical Analysis Systems, Inc., Camarillo, CA (US)

( * ) Notice: Subject to any disclaimer, the term of this patent is extended or adjusted under 35 U.S.C. 154(b) by 0 days.

(21) Appl. No.: 09/845,091

(22) Filed: Apr. 27, 2001

(65) Prior Publication Data

US 2002/0193287 A1 Dec. 19, 2002

(51) Int. Cl.$^7$ .......................... C07K 7/00; C07K 17/00; C12N 9/96; C12M 1/02; A61K 39/385
(52) U.S. Cl. ................. 530/300; 424/193.1; 424/194.1; 435/188; 435/302; 435/302.1; 530/350
(58) Field of Search ................................ 435/302, 188, 435/302.1; 530/300, 350; 424/193.1, 194.1

(56) References Cited

U.S. PATENT DOCUMENTS

| | | |
|---|---|---|
| 4,806,524 A | 2/1989 | Kawaguchi et al. |
| 4,902,502 A | 2/1990 | Nitecki et al. |
| 5,089,261 A | 2/1992 | Nitecki et al. |
| 5,266,488 A | 11/1993 | Ordahl et al. |
| 5,349,001 A | 9/1994 | Greenwald et al. |
| 5,359,030 A | 10/1994 | Ekwuribe |
| 5,446,090 A | 8/1995 | Harris |
| 5,468,478 A | 11/1995 | Saifer et al. |
| 5,556,788 A | 9/1996 | Kwan et al. |
| 5,583,200 A | 12/1996 | Larue et al. |
| 6,072,040 A | 6/2000 | Davé et al. .................. 530/412 |
| 6,165,981 A | 12/2000 | Flaa et al. .................... 514/21 |
| 6,248,869 B1 | 6/2001 | Morjana et al. |

FOREIGN PATENT DOCUMENTS

| | | |
|---|---|---|
| WO | WO 94/27156 | 11/1994 |
| WO | WO 96/10076 | 4/1996 |
| WO | WO 98/54218 | 12/1998 |
| WO | WO 98/54219 | 12/1998 |
| WO | WO 98/56900 | 12/1998 |

OTHER PUBLICATIONS

Abuchowski et al., "Alteration of Immunological Properties of Bovine Serum Albumin by Covalent Attachment of Polyethylene Glycol," The Journal of Biological Chemistry, Jun. 1977, pp. 3578–3581, vol. 252, No. 11.

Abuchowski et al., "Cancer Therapy with Chemically Modified Enzymes. I. Antitumor Properties of Polyethylene Glycol–Asparaginase Conjugates," Cancer Biochem Biophys., 1984, pp. 175–186, vol. 7, Science Publishers Inc., Great Britain.

Abuchowski et al., "Effect of Covalent Attachment of Polyethylene Glycol on Immunogenicity and Circulating Life of Bovine Liver Catalase," The Journal of Biological Chemistry, Jun. 10, 1977, pp. 3582–3586, vol. 252, No. 11.

Adams et al., "Cardiac Troponin I: A Marker with High Specificity for Cardiac Injury," Circulation, Jul. 1993, pp. 101–106, vol. 88. No. 1.

Antman, Elliot M., M.D., et al., "Cardiac–Specific Troponin I Levels to Predict the Risk of Mortality in Patients with Acute Coronary Syndromes," The New England Journal of Medicine, Oct. 31, 1996, pp. 1342–1349, vol. 335, No. 18.

Armour et al., "Cloning and Expression in *Escherichia coli* of the cDNA Encoding Human Cardiac Troponin I," Gene, 1993, pp. 287–292, vol. 131, Elsevier Science Publishers B.V.

Beauchamp et al., "A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin," Analytical Biochemistry, 1983, pp. 25–33, vol. 131, Academic Press, Inc.

Bodor et al., "Cardiac Troponin T Composition in Normal and Regenerating Human Skeletal Muscle," Clinical Chemistry, 1997, pp. 476–484, vol. 43, No. 3.

Bodor et al., "Development of Monoclonal Antibodies for an Assay of Cardiac Troponin–I and Preliminary Results in Suspected Cases of Myocardial Infarction," Clinical Chemistry, 1992, pp. 2203–2214, vol. 38, No. 11.

Eisenberg et al., "Troponin–Tropomyosin Complex: Column Chromatographic Separation and Activity of the Three Active Troponin Components with and without Tropomyosin Present," The Journal of Biological Chemistry, Aug. 10, 1974, pp. 4742–4748, vol. 249, No. 15.

Farah et al., "The Troponin Complex and Regulation of Muscle Contraction," The FASEB Journal, Jun. 1995, pp. 755–768, vol. 9, No. 9, The Federation of American Societies for Experimental Biology.

Hermanson, Greg T., Bioconjugate Techniques, 1996, Academic Press Inc., pp. 605–629.

(List continued on next page.)

Primary Examiner—Jon P. Weber
Assistant Examiner—Kailash C. Srivastava
(74) Attorney, Agent, or Firm—Christie, Parker & Hale, LLP

(57) ABSTRACT

The present invention provides methods for preparing, and compositions comprising, stabilized protein-polymer conjugates. More particularly, the present invention relates to the stabilization of individual and complexed subunits of multisubunit protein complexes by conjugation to polymers. Such conjugation acts to stabilize the specific subunit complexes in their native conformation in liquid medium.

18 Claims, No Drawings

OTHER PUBLICATIONS

Katre, Nandini V., "Immunogenicity of Recombinant IL–2 Modified by Covalent Attachment of Polyethylene Glycol," The Journal of Immunology, 1990, pp. 209–213, vol. 144, No. 1, The American Association of Immunolotgists.

Katus, Hugo A, M.D., et al., "Diagnostic Efficency of Troponin T Measurements in Acute Myocardial Infarction," Circulation, Mar. 1991, pp. 902–912, vol. 83, No. 3.

Kobayashi et al., "Structure of the Troponin Complex: Implications of Photocross–Linking of Troponin I to Troponin C Thiol Mutants," The Journal of Biological Chemistry, Feb. 25, 1994, pp. 5725–5729, vol. 269, No. 8, The American Society for Biochemistry and Molecular Biology, Inc.

Larue et al., "Cardiac–Specific Immunoenzymometric Assay of Troponin I in the Early Phase of Acute Myocardial Infarction," Clinical Chemistry, pp. 972–979, vol. 39, No. 6.

Larue et al., "New Monoclonal Antibodies as Probes for Human Cardiac Troponin I: Epitopic Analysis with Synthetic Peptides," Molecular Immunology, 1992, pp. 271–278, vol. 29, No. 2, Pergamon Press, Great Britain.

Leszyk et al., "Amino Acid Sequence of Bovine Cardiac Troponin I," Biochemistry, 1988, pp. 2821–2827, vol. 27, No. 8, The American Chemical Society.

Leszyk et al., "Cross–Linking of Rabbit Skeletal Muscle Troponin with the Photoactive Reagent 4–Maleimidobenzophenone: Identification of Residues in Troponin I that are Close to Cysteine–98 of Troponin C," Biochemistry, 1987, pp. 7042–7047, vol. 26, No. 22, American Chemical Society.

Marsh et al., "Determination of Substrates Using Poly(ethylene glycol)–Stabilized Dehydrogenase Enzymes by Microlitre Per Minute Flow Injection," Analyst, Apr. 1995, pp. 1091–1096, vol. 120.

Müller–Bardorff et al., "Improved Troponin T ELISA Specific for Cardiac Troponin T Isoform: Assay Development and Analytical and Clinical Validation," Clinical Chemistry, 1997, pp. 458–466, vol. 43, No. 3.

Ohman, E. Magnuse., M.D., et al., "Cardiac Troponin T Levels for Risk Stratification in Acute Myocardial Ischemia," The New England Journal of Medicine, Oct. 31, 1996, pp. 1333–1341, vol. 335, No. 18, Massachusetts Medical Society.

Pan et al., "Two Genetically Expressed Troponin T Fragments Representing α and β Isoforms Exhibit Functional Differences," The Journal of Biological Chemistry, Nov. 15, 1992, pp. 23052–23056, Col. 267, No. 32, The American Society for Biochemistry and Molecular Biology, Inc.

Sambrook et al., "Molecular Cloning : A Laboratory Manual Second Edition," 1989, Book 1, Sections 1.53–1.73, Cold Spring Harbor Laboratory Press.

Sambrook et al., "Molecular Cloning : A Laboratory Manual Second Edition," 1989, Book 1, Sections 2.82–2.107, Cold Spring Harbor Laboratory Press.

Sambrook et al., "Molecular Cloning : A Laboratory Manual Second Edition," 1989, Book 1, Sections 3.5–3.58, Cold Spring Harbor Laboratory Press.

Sambrook et al., "Molecular Cloning : A Laboratory Manual Second Edition," 1989, Book 2, Sections 8.3–8.51, Cold Spring Harbor Laboratory Press.

Sambrook et al., "Molecular Cloning : A Laboratory Manual Second Edition," 1989, Book 2, Sections 9.4–9.62, Cold Spring Harbor Laboratory Press.

Schaertl et al., "Separation and Characterization of the Two Functional Regions of Troponin Involved in Muscle Thin Filament Regulation," Biochemistry, 1995, pp. 15890–15894, vol. 34, No. 49, Accelerated Publications.

Scopes, Robert K., "Protein Purification Principles and Practice Second Edition," 1987, Springer–Verlag New York Inc.

Staprans et al., "Skeletal and Cardiac Troponins and Their Components," J. Biochem., 1972, pp. 723–735, vol. 72, No. 3.

Townsend et al., Human Cardiac Troponin T: Identification of Fetal Isoforms and Assignment of the TNNT2 Locus to Chromosome 1q., Genomics, 1994, pp. 311–316, vol. 21, Academic Press, Inc.

Tsuji et al., "Monomer of the B Subunit of Heat–Labile Enterotoxin from Enterotoxigenic *Escherichia coli* Has Little Ability to Bind to $GM_1$ Ganglioside Compared to Its Coligenoid," Microbiol. Immunol., 1995, pp. 817–819, vol. 39, No. 10.

Vallins, et al., "Molecular Cloning of Human Cardiac Troponin I Using Polymerase Chain Reaction," Federation of European Biochemical Societies, Sep. 1990, pp. 57–61, vol. 270, No. 1, 2, Elsevier Science Publishers B.V.

Zalipsky et al., "Evaluation of a New Reagent for Covalent Attachment of Polyethylene Glycol to Proteins," Biotechnology and Applied Biochemistry, 1992, pp. 100–114, vol. 15, Academic Press, Inc.

STABILIZATION OF CARDIAC TROPONIN I SUBUNITS AND COMPLEXES

BACKGROUND OF THE INVENTION

The present invention relates to the conjugation of individual and complexed subunits of multisubunit protein complexes with polymers to stabilize their conformation. More specifically, the present invention describes a method of stabilizing individual and complexed subunits via covalent conjugation to a natural or synthetic polymer. The present invention also relates to stabilized conjugates of cardiac troponin I and C, and methods for its preparation.

SUMMARY OF THE INVENTION

Proteins are composed of long chains of amino acids. The structure of proteins can be considered on four different levels. The primary structure refers to the specific order of amino acids in the polymer chain. The secondary structure refers to the interactions among and between the amino acids in the chain to form such structures as $\alpha$-helices and $\beta$-pleated sheets. The tertiary structure refers to the three-dimensional structure of the protein, which is also referred to as a protein's conformation. The quaternary structure refers to the spatial arrangement of individual polypeptides or subunits of multisubunit proteins.

The native conformation of a protein is only marginally stable. Thus, many proteins which are removed from their native environment and purified undergo conformational changes which can cause a loss of biological activity, such as enzyme activity or antibody binding capacity. In particular, the individual (uncomplexed) subunits of multisubunit protein complexes may undergo dramatic conformational changes when separated from the other subunits of the complex and stored in a liquid medium.

It is often desirable to separate the individual subunits of a multisubunit protein complex, for example to study or exploit the biological activity of each individual subunit. However, this may not be possible if the individual subunits undergo conformational changes in their uncomplexed state that alter their biological activity. Therefore, it is often desirable to stabilize specific subunit complexes of more than one, but less than all, subunits of a multisubunit protein. Accordingly, it is an object of the present invention to provide a method for stabilizing specific subunit complexes of multisubunit proteins.

Troponin is an example of a multisubunit protein complex which consists of three individual subunits; troponin T, troponin C, and troponin I. The troponin complex is involved in the calcium-sensitive switch that regulates the interaction of actin and myosin in striated muscles. Troponin T binds the troponin complex to tropomyosin, while troponin I is the inhibitory subunit of the complex, because it inhibits the actomyosin $Mg^{2+}$-ATPase. Whereas troponin (TnC), which binds $Ca^{2+}$, from skeletal muscle and cardiac muscle is identical, troponin I and T (TnI and TnT) from these two sources exist as different isoforms, each having a different amino acid sequences and thus a unique structure. Thus, cardiac troponin I (cTnI), cardiac troponin T (cTnT), and subunit complexes, such as cardiac troponin I and C (cTnIC) are of particular interest as cardiospecific markers.

The majority of the research into the troponin complex has centered around the regulatory function and structure of the troponin complex in skeletal muscle. The troponin complex assists in muscle contraction. The TnC molecule has four binding domains to bind divalent metal ions. The $Ca^{2+}/Mg^{2+}$ binding sites are in the C-terminal region and the $Ca^{2+}$ binding sites are in the N-terminal region. In studies of skeletal muscle, in the absence of $Ca^{2+}$, the N-terminus of TnI binds to the C-terminal region of TnC and to the globular C-terminal region of TnT. Thus, research indicates that TnI and TnC are anti-parallel and TnI and TnT are anti-parallel. The presence of calcium ion increases the C-terminal domain's affinity for the inhibitory and C-terminal regions of TnI. In addition, there is a hydrophobic surface in the N-terminal domain of TnC that represents a $Ca^{2+}$ dependent binding site for TnI and TnT. It has been proposed that the $Ca^{2+}$ dependent reactions relate to the regulatory mechanism and $Ca^{2+}$ independent interactions maintain the structural integrity of the complex. In order to study structure and function of the troponin complex in its regulation of skeletal muscle, cross-linking studies have been accomplished. See Farah, C. and Reinach, F. Review: The Troponin complex and regulation of muscle contraction. FASEB Journal 9 pp. 755–767 (1995). Covalent binding between TnC and skeletal muscle TnI has been formed between the carboxyl groups in the TnC and lysine groups in TnI using EDC. See Kobayoshi et al. (1994), Structure of the troponin complex: implications of photocross-linking of troponin I to troponin C thiol mutants. J. Biol. Chem. 269, 5725–5729. In addition, Leszyk et al. (1987) Cross-linking of rabbit skeletal muscle troponin with the photoactive reagent 4-malemidobenzophenone; identification of residues in troponin I that are close to cystein-98 of troponin C. Biochemistry 26, 7042–7047, reported that the main product of cross-linking between TnC and skeletal muscle TnI comprises segments derived from the N-terminal regulatory domain of TnC (residues 46 to 78) and the inhibitory region of skeletal TnI (residues 9–116).

U.S. patent application Ser. No. 08/865,468, filed on May 29, 1997, discloses that the majority of native cTnI in human serum after myocardial infarction (MI) is associated with TnC and TnT. The presence of TnI in a complex with other troponin subunits in MI patient serum increases its stability and protects it from further degradation. In addition, the troponin complex protects the sites where cardiac-specific antibodies bind. U.S. patent application Ser. No. 08/865,468, filed on May 29, 1997, also discloses methods to isolate the complex from MI patient serum.

The determination of the presence or amount of certain constituents or analytes is useful in the diagnosis of disease and physical well-being. Compositions which behave similarly to how constituents present in human bodily fluids behave, e.g., blood, blood serum, plasma, spinal fluid, and urine, are used in clinical laboratories. These compositions assist in the determination of whether the clinical instrumentation and procedures used by the laboratory to measure the constituents are accurate. These compositions are also used to calibrate the clinical devices which measure the amount or presence of the constituent in a sample. These compositions will be referred to hereinafter as control compositions or controls.

Rapid and simple tests that can be used to accurately diagnose the occurrence of myocardial infarction or distinguish other ischemic events such as unstable angina are extremely important. Cardiac troponin I (cTnI) and troponin T (cTnT) have recently become established as the markers of choice in evaluating cardiac distress. See for example, New England Journal of Medicine Volume 335 No. 18, pages 1342–1349, Antman et al. and pages 1333–1341, Ohman et al.

A variety of immunoassays have been developed that utilize antibodies that can distinguish between the three troponin subunits, and also between their different isoforms. Monoclonal and polyclonal antibodies have been designed and used in immunoassays which can detect the cardiac-specific epitopes formed by the unique amino acid sequence of cTnI. See for example, International Patent Application No. WO 96/10076; European Patent No. 394,819 B1; and Adams et al., Circulation 88:101–106 (1993). Larue et al., (Clin. Chem. 39:972–979 (1993)) describe an immunoenzyme assay that is capable of detecting cTnI in the concentration range of 0.2 to 20 μg/L in 30 minutes.

Immunoassays have also been described which are specific for TnT. See for example, Katus, et al., Circulation, 83(3):902–912 (1991). An immunoassay for TnT is also commercially available from Boehringer Mannheim Corporation (Indianapolis, Ind.).

Most immunoassays are designed to determine the concentration of a given marker in a patient's serum by comparing immunoassay results with the patient's serum to those obtained with controls of known concentration. One limitation in the development of immunoassays for individual troponin subunits involves the instability of the troponins in their uncomplexed state. Accordingly, there is a need for stabilized compositions of tronponin subunit complexes that can be stored for extended periods of time, while retaining antibody binding capacity for use as control reagents in cTnI and/or cardiac troponin IC complex (cTnIC) immunoassays.

In vitro stabilized solutions for cardiac markers have been disclosed. U.S. Pat. No. 5,583,200 and Bodor et al., (1992) Development of Monoclonal Antibodies for an Assay of Cardiac Troponin-I and Preliminary Results in Suspected Cases of Myocardial Infarction, Clin. Chemistry 38, (11) 2203–2214 at 2204 disclose stabilized troponin T and/or troponin I using troponin C and calcium ion. U.S. Pat. No. 5,583,200 discloses that serum may be added. U.S. patent application Ser. No. 08/874,566, filed Jun. 13, 1997, discloses improvements in stabilizing the troponin T or troponin IC complex and discloses solutions useful as calibrators or controls for diagnostic assays measuring troponin. U.S. patent application Ser. No. 08/564,526 and U.S. patent application Ser. No. 08/865,468, filed May 29, 1997, also disclose the effect of TnC upon the immunological and biological activity and non-specific binding of the CNBr-cTnI isoform and other fragments. U.S. patent application Ser. No. 08/564,526 discloses the activity of the complex formed by the CNBr-cTnI isoform, TnC and TnT as useful in immunoassays.

The calibrators and controls in Behring's OPUS® assay are a lyophilized preparation of human cardiac troponin I in processed bovine calf serum with stabilizers. The reconstituted products are stable for seven days when stored at 2 to 8° C. The calibrators and controls in Sanofi Pasteur's troponin I assay are a lyophilized preparation in a buffered human serum matrix. The reconstituted calibrators must be used within fifteen minutes after complete reconstitution, but may be aliquoted and stored frozed at −20° C. for up to about six months. The calibrators and controls in the Dade troponin I assay are provided frozen. When thawed the product is stable for thirty days when stored at 2to 8° C.

Stabilization of proteins via covalent conjugation to various polymers has been described. See, for example, U.S. Pat. Nos. 4,902,502; 5,468,478; 4,806,524; Katre et al., J. Immunol. 144:209–213 (1990); Abuchowski et al., J. Biol. Chem. 252:3582–3586 (1977). The properties conferred on the conjugated protein have been cited as increased in vivo half life, increased stability in solution, increased solubility, decreased susceptibility to proteases and decreased immunogenicity and antigenicity. For example, Nitecki et al. (U.S. Pat. No. 5,089,261) describe conjugating interleukin-2 to polyethylene glycol (PEG) to reduce immunogenicity.

In addition to stabilization of proteins via covalent conjugations to polymers, it has also been demonstrated that synthetic polymers are capable of providing a stabilizing effect via an ionic interaction with proteins. For example, Marsh and Danielson (Analyst 120:1091–1096 (1995)) have described that the addition of PEG to an aqueous solutions of the multisubunit enzyme lactate dehydrogenase enhances the ability of the enzyme subunits to remain complexed.

The present invention relates to the finding that covalent conjugation of protein individual and complexed subunits of multisubunit proteins to polymers stabilizes the protein subunits, i.e., the subunit complex maintains its native conformation in a liquid medium for a longer period of time than the equivalent unconjugated subunit complex. In a preferred embodiment, the present invention also relates to cTnIC polymer conjugates which exhibit stabilized antibody binding capacity.

DETAILED DESCRIPTION OF THE INVENTION

The present invention concerns stabilization of specific individual and complexed subunits of multisubunit protein complexes. Stabilization is accomplished by conjugating the individual and complexed subunits to a polymer. The stabilizing effect of conjugation allows the individual and complexed subunits to be stored in liquid medium for longer periods of time than the equivalent unconjugated or "free" individual and complexed subunits. This greatly enhances the shelf life of the composition. In a preferred embodiment, the stabilized subunit complex is the cTnIC complex, which in its unconjugated form is less stable in liquid medium.

Polymers which are useful in the present invention can be naturally occurring or synthetic. Whereas certain synthetic polymers may be preferred for stabilization of individual subunits such as free cTnI and subunit complexes such as cTnIC, as will be discussed below, natural polymers such as serum proteins are preferred for stabilization of cTnT. A particularly preferred class of synthetic polymer is PEG. Other suitable polymers include, but are not limited to, polyalkylene glycols, polyoxyethylated polyols, polyvinylpyrrolidone, polyhydroxyethyl methacrylate, polyvinyl alcohols, polyurethane, and derivatives thereof. As used herein, the term "conjugated" refers to proteins bound to molecules for stabilization, such as polymers, and may also be bound to the other subunits found in the naturally occurring protein, and "unconjugated" refers to unbound proteins and protein subunits bound to other subunits found in naturally occurring protein but not to other molecules for stabilization.

The polymers which are useful in the present invention may vary in molecular weight, and must have a molecular weight which is sufficient to stabilize the subunit complexes. This generally requires that the polymer have a molecular weight between 100 and 200,000, more preferably between 1000 and 40,000, and most preferably between 2500 and 10,000. In a particularly preferred embodiment, PEG having a molecular weight of 5000 is used.

In order to conjugate the polymer to the individual protein subunits, it should be in an "active" form, which means it must contain at least one reactive group capable of reacting with pendant groups on the protein to form a covalent linkage. When the polymer is PEG, a preferred active form is monomethoxy-PEG p-nitrophenyl carbonate.

The ratio of protein to polymer in the conjugation reaction must be sufficient to stabilize the individual subunit. This generally requires that the polymer is provided in a molar concentration which is at least equivalent to the molar concentration of the individual subunit. Preferably, the polymer is provided in excess to ensure that a sufficient number of polymers are covalently attached to the individual subunits. When the polymer is conjugated with a subunit complex, the polymer is provided in a molar excess of the protein ranging from about 1× to about 20,000×, preferably, from about 770× to about 11,550×, more preferably from about 6000× to about 8000×. In a particularly preferred embodiment, the molar excess is 7700×. When the polymer is conjugated with an individual subunit, the polymer is provided in a molar excess of the protein ranging from about 1× to about 20,000×, preferably, from about 100× to about 3000×. In a particularly preferred embodiment, the molar excess is 2400×.

As an alternative to polymers, monomers (at least some of which are in an active form) can be used to form the protein-polymer conjugates of the present invention, which may polymerize during conjugation and may even attach directly to the protein subunit to afford the desired stability.

Another aspect of the present invention relates to compositions that consist of individual and complexed subunits-polymer conjugates in liquid medium. Suitable liquid media include water, aqueous solvents, serum, and mixtures thereof. Preferably, the liquid medium is mammalian serum, and more preferably, it is human serum. Other excipients, such as salts, buffers, proteins, polymers, carbohydrates, preservatives and reducing agents may also be added to the liquid medium.

A preferred embodiment of the present invention relates to stabilized conjugates of cTnIC which are useful as control reagent compositions for immunoassays. Preferably, the cTnIC conjugates are formed by conjugating a synthetic polymer, such as PEG, to the protein's pendant amine groups. Because cTnIC's amine-containing lysine residues are not located in the cardiac-specific N-terminal portion of the protein, conjugation to PEG does not appreciably affect the ability of the cTnIC to bind to cardiac-specific anti-cTnI, anti-TnC, or anti-cTnIC antibodies.

In another embodiment, the present invention relates to a method of stabilizing individual and complexed subunits of multisubunit proteins by providing a solution of the subunit(s), adding a multifunctional crosslinking agent to activate the subunit(s), then simultaneously or subsequently adding a polymer to effect conjugation of the subunit(s) to the polymer via the crosslinking agent. This method of stabilization is particularly preferred for conjugating serum proteins such as albumin to cTnIC via glutaraldehyde, although it is also useful for other combinations of polymers and subunits as described herein, as well as with other multifunctional crosslinking agents.

The term "stabilized" as used herein means that the conformation of the protein subunits when suspended in a liquid medium is maintained for a longer period of time than the equivalent unconjugated or "free" subunits. Stabilization can be measured as a function of the subunits' ability to retain at least one biological activity or epitopic recognition when suspended in a liquid medium and stored for a period of time, relative to the subunits in their native state. For example, a protein-polymer conjugate would be considered stabilized if it maintained a level of about 50% of at least one of its biological activities upon storage in a liquid medium, compared to the free protein or subunit complexes. Biological activity of protein subunits can be any biological characteristic attributed at least in part to those particular subunits of a multisubunit complex, such as enzyme activity, ligand binding capacity, substrate recognition, antibody binding, nucleic acid binding and the like.

The hydrophobic interactions between subunits of multisubunit proteins (i.e., a protein's quaternary structure) lend stability to the complex, and also to the conformation of the individual subunits within the complex. Accordingly, isolation of some subunits from a multisubunit protein complex can cause many subunits to undergo conformational changes. For example, individual subunits of multisubunit E. coli enterotoxin have been shown to lose ligand binding capacity when separated from the native complex (Tsuji et al., Microbiol. Immunol. 39:817–819 (1995)).

Since a protein's biological activity depends on its conformation, stability of a protein can be measured as a function of the protein's biological activity. For example, specific ligands such as antibodies that recognize the native conformation of a protein can be used to measure changes of the conformation.

Specific subunit complexes of multisubunit proteins may be useful for a variety of purposes, such as for studying or exploiting the biological activities of individual subunits or complexes of a few subunits in a multisubunit protein complex. For example, in immunoassays, where target specificity can be achieved only by targeting antibodies to a particular subunit complex of a multisubunit protein complex, the individual subunit complex is useful as a control reagent for the immunoassay.

Additionally, subunit complexes of proteins are useful for controls for in vitro diagnostic use.

Cardiac Troponin I (cTnI)

Troponin is a three-subunit complex of troponin I, T, and C. The cardiac isoform of troponin I (cTnI) is an ideal target for the study and diagnosis of acute myocardial infarction.

U.S. Pat. No. 6,072,040 relates to cTnI-polymer conjugates and methods for the preparation thereof. More particularly, conjugation of cTnI to polymers which act to prevent the uncomplexed cTnI subunit from losing its native conformation and thereby maintaining its binding capacity for cTnI-specific antibodies during storage in a liquid medium is described.

The nucleic acid sequence of the gene which codes for cTnI and its amino acid sequence have previously been described by Armour et al. (Gene 131:287–292 (1993); GenBank Accession No. M64247).

The term cTnI as used herein also intends fragments of cTnI that retain at least one epitope which is recognizable by a monoclonal or polyclonal antibody (or fragment thereof) that preferentially binds to cardiac isoforms of troponin I. Also included in the term cTnI are: polypeptides that have amino acid substitutions, deletions or insertions relative to the native or naturally occurring amino acid sequence of cTnI; and fusion proteins that contain all or a fragment of cTnI linked to another protein.

The cardiac isotype of the myofibrillar contractile protein, Troponin I, is uniquely located in cardiac muscle. TnI is the inhibitory subunit of troponin, a thin filament regulatory protein complex, which confers calcium sensitivity to the cardiac and striated muscle. Troponin I exists in three isoforms: two skeletal TnI (fast and slow) isoforms (Molecular Weight: 19,800 daltons) and a cardiac TnI isoform with an additional 31 residues (human TnI) on the N-terminus resulting in a molecular weight of 23,000 daltons.

Cardiac TnI is found in human serum rapidly (within approximately 4 to 6 hours) following a myocardial infarction. It reaches a peak level after approximately 18 to 24 hours and remains at elevated levels in the blood stream for up to 6 to 7 days. Thus, immunoassays which can test for human cTnI are valuable to the medical community and to the public.

It is desirable to use an immunologically reactive human cTnI isoform comparable to that found in MI patient serum as a marker. International Patent Application No. WO 98/54219 describes the findings that MI patient serum contains TnI fragment(s) which are the result of the C-terminal processing of cTnI molecule. The high sequence homology found in the C-terminal region between cardiac TnI and skeletal muscle TnI (Larue et al. 1992 Molec. Immunology 29, 271–278, Vallins et al. 1990 FEBS Lett. 270, 57–61, Leszky et al. 1988 Biochemistry 27, 2821–2827) produce TnI antibodies directed against this region having non-cardiac specificity.

Currently cTnI immunoassays are commercially available from several sources, including Dade International, Bayer, Behring Diagnostics, and Sanofi Pasteur Diagnostics. For example, Dade International manufactures the Stratus™ and Dimension RXL™ Cardiac Troponin-I assay and Bayer manufactures the ACS-180™ and Centaur™ systems.

Native intact human cTnI is difficult to obtain because of the scarcity of human heart tissue and is highly subject to proteolytic degradation during purification. Recombinant cardiac TnI, unlike the native human cTnI, can be produced and purified in acceptable quantities. As described by Dade, in International Application, WP 98/54219, the primary structure of r-cTnI contains 226 amino acids; 209 of them represent the cTnI sequence. In addition to the primary sequence of cTnI, r-cTnI, there is a leading sequence of 8 amino acids on the N-terminus, and a tail sequence of 9 amino acids on the C-terminus. The primary structure of the r-cTnI molecule has methionine residues at positions –7, –4, 0, 153, 154, 200, and 211.

The sequence of full length cardiac troponin I has been described in Armour, K. L. et al., (1993) Cloning and Expression in *Escheria Coli* of the cDNA Encoding Human Cardiac Troponin I, *Gene*, 131 (2):287–292).

U.S. patent application Ser. No. 08/564,526 discloses the use of a human cTnI fragment generated from human r-cTnI by chemical cleavage. The cleavage of r-cTnI by cyanogen bromide (CNBr) results in a major polypeptide of 153 amino acids, hereinafter referred to as the CNBr-cTnI isoform. The CNBr-cTnI isoform represents 73% of the primary structure of human cTnI and is immunologically more reactive than r-cTnI. The purified CNBr-cTnI isoform has an average of 3 to 4 times more reactivity than r-cTnI and lower non-specific binding, as measured by radial partition immunoassay. The molecular size of the CNBr-cTnI isoform is comparable in molecular weight to the major degradation product of native cardiac TnI in MI patient serum.

It is desirable to use an immunologically reactive human cTnI isoform comparable to that detected in MI patient serum. The availability of r-TnI can facilitate the production of cardiac cTnI isoforms. Moreover, since most of the known human cardiac specific TnI antibodies have their epitopes located approximately in the first 75% of the TnI molecule, that portion of the TnI molecule will function as a cTnI isoform in most immunoassays.

The CNBr-cTnI isoform can be used as calibrators or controls in various cTnI immunoassays, for examples. As described in International Patent Applications Nos. WP 98/56900 and WO 98/54218.

Cardiac TnI is also released after acute myocardial infarction. In contrast to cTnT, cTnI has never been found in a healthy population, which includes marathon runners, in people with skeletal disease, or in patients undergoing non-cardiac operations. Thus, cTnI is a more specific marker for the diagnosis of AMI than other serum proteins.

Cardiac Troponin T (cTnT)

Like cTnI, cTnT is also useful as a marker for the study of acute myocardial infarction. U.S. Pat. No. 6,072,040 describes to cTnT-polymer conjugates and methods for the preparation thereof. Similarly to cTnI, conjugation of cTnT to polymers also acts to maintain cTnT's native conformation. After myocardial infarction, cTnT levels increase and remain elevated for an extended period. However, it has been reported that in a variety of disease states, cTnT is also expressed in skeletal muscle, which contributes to a lack of cardiospecificity of this protein. Furthermore, uremia, a condition associated with cardiomyopathy, is associated with elevated cTnT. Thus, a lack of absolute cardiospecificity makes this marker less than optimal for use in the early diagnosis of acute myocardial infarction (AMI).

The nucleic acid sequence of the gene which codes for cTnT and its amino acid sequence have previously been described by Townsend, et al., Genomics, 21(2): 311–316 (1994); GenBank Accession No. X74819.

The term cTnT as used herein also intends fragments of cTnT that retain at least one epitope which is recognizable by a monoclonal or polyclonal antibody (or fragment thereof) that preferentially binds to cardiac isoforms of troponin T. Also included in the term cTnT are: polypeptides that have amino acid substitutions, deletions or insertions relative to the native or naturally occurring amino acid sequence of cTnI; and fusion proteins that contain all or a fragment of cTnT linked to another protein.

Troponin T with a molecular weight of 39,000 kD is part of the troponin-tropomyosin complex of the thin filament that is part of the muscle contractile apparatus and that contains actin and tropomyosin regulatory elements. Skeletal muscle studies of TnT have found that TnT is structurally asymmetric. Its terminal globular C-terminal domain (TnT-2) mediates its interaction with TnI and TnC. TnT-I at the N-terminal domain interacts with tropomyosin. See, Farah, C. and Reinach, F. (1995) Review: The Troponin complex and regulation of muscle contraction. *FASEB* Journal 9 755–767. It has been reported that skeletal TnT is cleaved into the skeletal TnT-I and TnT-2TnI-TnC fragments by mild proteolysis. Schaertl, S. et al. (1995) Separation and Characterization of the Two Functional Regions of Troponin Involved in Muscle Thin Filament Regulation. Biochemistry 34 (49) 15890–15894. TnT serves as a link between the tropomyosin backbone and the Troponin IC complex. TnT has isotypes in cardiac and fast and slow skeletal muscles. It appears in serum about 3 hours after the onset of chest pain and remains elevated for at least 10 days following MI. Despite its lack of complete cardiac specificity it can be useful because of its rapid appearance into the bloodstream. Troponin T can be obtained as described in J. Biochem. 72: pages 723–735 (1972) or *J. Biol. Chem.* 249: 4742–4748, or purchased commercially. TnT gene promoter and derivatives thereof are disclosed in U.S. Pat. No. 5,266,488. TnT isoforms of skeletal muscle show variation in a given species in about a 30 amino acid region of the amino terminus and about a 14 amino acid region of the carboxy terminus (Pan, B. S. and Potter, J. D. (1992) Two Genetically Expressed Troponin T fragments Representing α and β Isoforms Exhibit Functional Differences. *Journal of Biological Chemistry* 267 (82) 23052–23056).

Troponin C (TnC)

Unlike troponin I and troponin T, troponin C from skeletal and muscle tissue is identical. That is, cTnC and sTnC are the same. Therefore, the TnC subunit alone is not a good marker for AMI, but together with cTnI or cTnT, can serve as a marker to MI. For example, the cTnI and TnC subunits together form an epitope recognized by the antibody, thereby serving as a marker for acute myocardial infraction (AMI). Similarly to cTnI, conjugation of TnC to polymers also acts to maintain TnC's native conformation.

The term TnC as used herein also intends fragments of TnC that retain at least one epitope which is recognizable by a monoclonal or polyclonal antibody (or fragment thereof) that preferentially binds to cardiac isoforms of troponin C. Also included in the term TnC are: polypeptides that have amino acid substitutions, deletions or insertions relative to the native or naturally occurring amino acid sequence of cTnI; fusion proteins that contain all or a fragment of TnC linked to another protein; and troponin C subunits that isolated from skeletal or other tissues.

Cardiac Troponin IC (cTnIC)

The cardiac isoform of the subunit complex troponin I and troponin C (cTnIC) is an ideal target for the study and diagnosis of acute myocardial infarction. The cTnI subunit is a suitable target for identification of acute myocardial infarction and the TnC subunit provides stability to the cTnI subunit.

The term cTnIC as used herein also intends fragments of cTnIC that retain at least one epitope which is recognizable by a monoclonal or polyclonal antibody (or fragment thereof) that preferentially binds to cardiac isoforms of troponin I or troponin C (or both). Also included in the term cTnIC are: polypeptides that have amino acid substitutions, deletions or insertions relative to the native or naturally occurring amino acid sequence of cTnIC; and fusion proteins that contain all or a fragment of cTnIC linked to another protein.

The troponin I and C subunits may be covalently bound to each other, for example, through cross-linking agents or peptide linkages, or noncovalently associated. Either subunit may be native or recombinant and may be full-length or truncated (fragmented). While some uncomplexed troponins can be found in human serum after a myocardial event, most cardiac specific troponin is found as complex. It has been found that the TnI in the cTnIC complex is degraded by proteolytic cleavage at the C-terminal end to provide an 18,000 kD fragment and a 14,000 kD fragment. Generally the 14,000 kD fragment is cleaved from the 18,000 kD fragment. After the cleavage to the 18,000 fragment, an N-terminus proteolytic cleavage occurs at the carboxyl side of Arg 26, thus eliminating the first 26 amino acids of the N-terminus.

Isolating Individual Subunits

Protein subunits and subunit complexes such as cTnI, cTnIC, and cTnT, can be isolated from their natural source in human or animal tissue, or they can be prepared using recombinant techniques. Recombinant techniques are well known in the art and involve isolation and/or synthesis of a polynucleotide encoding all or a fragment of the protein subunit and cloning into a suitable bacterial or eukaryotic expression vector. Such techniques are described in a variety of references, including but not limited to, Molecular Cloning: A Laboratory Manual, 2nd ed., Vol. 1–3, eds. Sambrook et al. Cold Spring Harbor Laboratory Press (1989). After insertion of the vector into a suitable host cell and expression of the desired protein subunit, the protein subunit can be isolated and purified using known techniques. See, for example, Scopes Protein Purification: Principles and Practice, 2nd Ed., Springer-Verlag, New York (1987).

In particular, cTnI can be isolated from heart muscle and substantially purified as described for the cTnI subunit in International Patent Application No. WO 94/27156. Therein, a procedure is given for affinity purification of cTnI on a troponin C affinity column. Human heart is trimmed of excess fat and valves and cut into 1 cm pieces at 4° C. The resulting tissue is homogenized in one portion with 750 ml extraction buffer (75 mM Tris buffer, pH 8.0, containing 8 M urea, 15 mM mercaptoethanol and 1 mM calcium chloride) at ambient temperature. The homogenate is centrifuged for 30 minutes at 7000×g and the supernatant liquid is filtered through cheesecloth to remove particulate matter. Troponin C coupled to a solid support gel is equilibrated in extraction buffer, and the heart extract is added to the equilibrated troponin C-gel. The resulting suspension is allowed to stir for 80 minutes at ambient temperature and then centrifuged 20 minutes at 7000×g. The pelleted gel is transferred to a column with extraction buffer. The column is washed at ambient temperature with a total of 700 ml of extraction buffer and the purified troponin I is then eluted from the column with elution buffer (75 mM Tris buffer, pH 8.0, containing 8 M urea, 15 mM mercaptoethanol, and 10 mM ethylenediamine tetraacetic acid).

The cTnT subunit and cTnIC subunit complex can be prepared as generally described above for cTnI, or it may be commercially obtained from a variety of companies such as Research Diagnostics, Inc., Flanders, N.J.; and HyTest, Turku, Finland.

TheTnIC complex can be prepared by completing TnC to cTnI. For example, 1-ethyl-3-[3-dimethylaminopropyl] carbondiimide hydrochloride (EDAC) and N-hydroxysuccinimide(NHS) is used to activate the carboxyl end of cTnC, forming an active ester, cTnC-NHS. β-mercaptoethanol is added to inactivate excess EDAC. TnI is added to the solution containing cTnC-NHS, resulting in a peptide bond between TnI and cTnC, forming a cTnIC complex, and releasing NHS.

Individual subunits of multisubunit protein complexes other than troponin can also be prepared as described above or by other known methods. In particular, individual subunits can be isolated from their natural source in biological samples by first separating the subunits, then using affinity chromatography with specific antibodies or other subunits of the complex.

Analyzing Subunit Complexes

In the present invention, polymer conjugation is used to stabilize the conformation of protein subunits. Before proceeding with conjugation, it is preferable to first make sure the protein subunit preparation has the desired conformation. In particular, after isolation of the specific subunit complexes of interest from multisubunit complexes, it is desirable to confirm that the isolation procedure did not adversely affect the conformation of the subunits. This can most easily be accomplished by determining whether the individual protein complex still has an acceptable level of the desired biological activity. For example, when the protein subunit is ultimately to be used as a control reagent in an immunoassay, antibody binding capacity should be determined. Testing the binding capacity of a protein for a particular antibody can be accomplished using known techniques. When the individual protein subunit is cTnI/cTnT, cardiac-specific cTnI/cTnT antibodies are used to determine antibody binding capacity. Cardiac-specific anti-cTnI/cTnT antibodies refers to antibodies that have a substantially greater binding affinity for cTnI/cTnT than for other troponins or skeletal forms of cTnI/cTnT. Such antibodies to cTnI have been previously described. See, inter alia, Katus et al., European Patent No. EP 394,819; Takahashi et al., International Patent Application No. WO 96/10076; Larue et al., Clin. Chem. 39:972–979 (1993); and Bodor et al., Clin. Chem. 38:2203–2214 (1992). Antibodies which are specific for cTnT have also been described. See for example, Bodor, et al., Clin. Chemistry, 43(3):476–484 (1997), which describes a polyclonal goat anti-cTnT antibody (G136-C; Fortron BioScience, Morrisville, N.C.) which was developed against the N-terminal amino acids 3–15 of human cTnT and which reportedly reacts <0.4% with skeletal isoforms.

In addition, Muller-Bardorff, et al. (Clin. Chemistry, 43(3) 458–466 (1997)) describe a monoclonal antibody pair (M7 and M11.7) which can be used in a sandwich assay for cTnT which reportedly cross reacts <0.3% with skeletal isoforms.

Polymers

Stabilization of protein individual and complexed subunits is achieved by conjugating the protein subunits to a polymer to prevent conformational changes of the protein subunits in the unconjugated state and thus loss of biological activity. The polymers of the present invention must have a high enough molecular weight to effectively stabilize the conformation of the protein subunit. Preferably, the molecular weight is between 100 to 200,000, more preferably between 1000 and 40,000, and most preferably between 2500 and 10,000. In a particularly preferred embodiment, the polymer molecular weight is 5000.

The polymer may be already formed prior to conjugation to the protein subunits (i.e., the monomeric units comprising the polymer may already be covalently attached), or in the alternative, the polymer may be formed during conjugation by using monomeric units such as monosaccharides, amino acids, or alkyl groups (C2 to C20 substituted or unsubstituted, branched or unbranched, saturated, partially saturated or unsaturated) which are polymerized (covalently attached to one another) during conjugation to the protein, or directly attached to the protein in their monomeric form. In any event, the term polymer and polymer-protein conjugate as used herein is intended to cover any of the aforementioned variations.

The polymer can be naturally occurring or synthetic. Examples of naturally occurring polymers include proteins, glycopeptides, polysaccharides such as dextran and lipids. In the case of cTnIC, the polymer is preferably a synthetic polymer. Examples of synthetic polymers which are suitable for use in the present invention include, but are not limited to, polyalkyl glycols (PAG) such as polyethylene glycol (PEG), polyoxyethylated polyols (POP) such as polyoxyethylated glycerol (POG), polytrimethylene glycol (PTG), polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, or co-polymers of two or more different synthetic monomers.

The synthetic polymers of the present invention have the following generic structure:

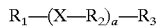

where $R_1$ and $R_3$ are the same or different and are H, $H_3C$, OH, $R_2$ or a reactive group (as described below); where $R_2$ is a linear or branched substituted or unsubstituted alkyl group; where X is O (in which case the synthetic polymer may be a polyoxyalkylene) or X is NH(C=O) (in which case the synthetic polymer may be a polyamine), or X is absent (in which case the synthetic polymer may be a polyalkylene); and a is an integer between 1 and 1000. Although hydrophilic polymers are preferred, it is also possible to use hydrophobic polymers, such as activated suberate or proprionate derivatives, or mixtures of hydrophilic or hydrophobic polymers.

A preferred class of synthetic polymers are the polyethylene glycols given by the formula:

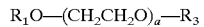

where $R_1$, $R_3$ and a are as described above. The term polyethylene glycol (PEG) includes both unsubstituted ($R_1$=H and $R_3$=OH) as well as substituted polyethylene glycol.

Naturally occurring proteins which are preferred for conjugation to cTnIC are serum proteins, such as albumin. For convenience, the naturally occurring protein used for conjugation to cTnIC can actually be a heterogeneous mixture of proteins, such as one which would be found in animal sera (for example, bovine or human), or in a synthetically produced serum substitute.

Polymer Activation

In order to conjugate the protein subunit to a polymer (which is either already polymerized or in its monomeric form at the time of conjugation), the polymer may first need to be activated. Activated means the preliminary attachment of a reactive group onto the polymer. A polymer which has been activated, as well as a polymer which already contains at least one reactive group is referred to as being active. Many synthetic polymers do not normally contain reactive groups which will react with a protein's pendant groups. For example, unsubstituted PEG has a hydroxyl group at each end of the linear polymer chain, one or both of which must first be activated before conjugation to a protein. To prevent the potential for cross-linking, it is desirable to activate only one of PEG's two hydroxyl termini to form a monofunctional substituted PEG. This can be accomplished by blocking one of the two hydroxyl groups with a methoxy group to form monomethoxypolyethylene glycol (mPEG).

Techniques for activating polymers prior to protein conjugation are known to those skilled in the art. See, for example, Greg T. Hermanson, Bioconjugate Techniques, p. 605–619 (1996) Academic Press. For example, activation of hydroxyl groups in PEG or mPEG as well as in other natural or synthetic polymers, can be accomplished using trichloro-s-triazine (TsT; cyanuric acid). (See, inter alia, Abuchowski et al., J. Biol. Chem. 252:3582–3586 (1977) and Abuchowski et al., J. Biol. Chem. 252:3578–3581 (1977)). Another method of activating hydroxyl groups is through formation of an amine reactive N-hydroxyl succinimidyl-(NHS) or p-nitrophenyl (Np) carbonate active ester. See Zalipsky et al., Biotechnol. Appl. Biochem. 15:100–114 (1992).

Similar activation can be achieved when the hydroxyl-containing polymer is first reacted with a cyclic anhydride (succinic or glutaric anhydride) and then the formed carboxyl modified product is coupled with N-hydroxyl succinimide in the presence of carbodiimides resulting in succinimidyl succinate or glutarate type active esters. See Abuchowski et al., Cancer Biochem. Biophys. 7:175–186 (1984).

A further method for activating a polymer's hydroxyl groups is through formation of an imidazolyl carbamate intermediate by reaction with N,N'-carbonyldiimidazole (CDI). The CDI-activated polymer reacts with amine groups of protein to form a stable N-alkyl carbamate linkage identical to that formed with succinimidyl carbonate chemistry described above. See Beauchamp et al., Anal. Biochem. 131:25–33 (1983).

For additional methods on activating synthetic polymers, such as PEG, see inter alia, U.S. Pat. Nos. 5,349,001; 5,359,030; and 5,446,090.

When the polymer to be conjugated to the protein subunits is a natural polymer such as a serum protein, it is generally preferred to activate the protein subunits by attachment of a multifunctional crosslinking agent as is more fully described in the following section.

Polymer-protein Conjugation

After activation of the polymer (if necessary), the polymer is conjugated to the protein subunits. In general, polymers can be covalently attached to proteins via pendant groups in the protein chain, such as primary amino groups, carboxyl groups, aromatic rings, or thiol groups, all of which may already be present, or can be added by preliminary chemical modification of the protein or by modifying a protein's amino acid sequence, using known molecular biology methods. One of the most frequently used and convenient methods involves attachment of the polymer to the protein's free amino groups in lysine residues ($\epsilon$-amino group) or to the protein's N-terminal amino acid ($\alpha$-amino group). This approach is preferred when the protein's amino groups are located in segments of the protein which are not crucial to maintaining the desired biological activity, such as is the case with cTnIC. The discussion which follows outlines two representative embodiments of the present invention. It is to be noted that the methodologies presented for cTnI are equally applicable for other protein subunit complexes.

The ratio of polymer to protein to be used to carry out the conjugation depends on the characteristics (structure, size, charge, reactivity) of the polymer, as well as the characteristics (number and location of pendant groups, nature of the biological activity) of the individual subunit complex. This generally requires that the polymer is provided in a molar concentration which is at least equivalent to the molar concentration of the individual subunit. Preferably, the polymer is provided in excess to ensure that a sufficient number of polymers are covalently attached to the protein to be stabilized. When the polymer is conjugated with a subunit complex, the polymer is provided in a molar excess of the protein ranging from about 1× to about 20,000×, preferably, from about 770× to about 11,550×, more preferably from about 6000× to about 8000×. In a particularly preferred embodiment, the molar excess is 7700×. When the polymer is conjugated with an individual subunit, the polymer is provided in a molar excess of the protein ranging from about 1× to about 20,000×, preferably, from about 100× to about 3000×. In a particularly preferred embodiment, the molar excess is 2400×.

cTnIC-polymer Conjugates

Since the cardiac-specific cTnI segment contains no lysine residues, it is possible to conjugate polymers to amino groups located elsewhere on the protein without appreciably affecting the ability of the cTnIC-PEG conjugate to bind to cardiac-specific anti-cTnI antibodies.

In the case of cTnIC and PEG, the preferred ratio is between 1 and 20,000 moles of active PEG per mole of cTnI, more preferably between 770 and 11,550, and most preferably between 6000 and 8000. The resultant cTnIC-PEG conjugate is considered stable if it retains at least 85% of its biological activity when stored at 4° C. for a period of about 30 days. In the case of cTnIC, biological activity refers to the ability of cTnIC to be recognized by cTnI-specific, cTnC-specific, or cTnIC-specific antibodies. The cTnIC-PEG conjugate is preferentially stored at temperatures ranging from −20° C. to 37° C., more preferably between about 2° C. to about 8° C., and even more preferably between about 4° C. to about 25° C. The cTnIC-PEG conjugate may also be lyophilized or stored under an inert gas such as argon, nitrogen, and the like.

In addition to conjugations which involve preactivation of the polymer, it is also possible to effect conjugation via a crosslinking agent. The crosslinking agent is preferably multifunctionally active and more preferably difunctionally active, which means that it contains more than one (multi-) or two (di-) reactive groups. The crosslinking agent can be one of the synthetic polymers described above which has been activated to contain two or more reactive groups, which can then be used as a linker to conjugate the protein subunit to another synthetic or natural polymer.

The crosslinking agent may also be a more conventional chemical crosslinking agent, including but not limited to, glutaraldehyde, formaldehyde, divinyl sulfane, carbodiimides, epoxides and imidazole. In the case of cTnIC, glutaraldehyde is preferred.

Protein-polymer Conjugate Compositions

Protein-polymer compositions can be formulated by diluting, dissolving or concentrating and rediluting the protein-polymer conjugate in a suitable liquid medium, such as water, aqueous solvents, serum, or mixtures thereof. Excipients can also be added to the liquid medium to further optimize the formulation. For example, cyclodextrin or other carbohydrates can be added to the protein-polymer conjugate to inhibit the rate of intermolecular aggregation during storage in the liquid medium.

Other optional components include, but are not limited to, casein, albumin, gelatin or other proteins. Buffers can be added to stabilize the pH of the liquid medium. Protease inhibitors such as phenyl methyl sulfonyl fluoride, leupeptin, pepstatin may also be included. Preservatives such as amphotericin B, cycloheximide, chloramphenicol, bacitracin, gentamicin, chloroheximide, sodium azide, trimethoprim, sulphomethaxozole may also be included. Additionally, reducing agents such as glutathione may be added.

It may also be desirable to sterilize the protein-polymer conjugate composition after formulation, such as by means of filtration. Filtration may be accomplished by passing the protein-polymer conjugate composition through a suitable size control device, such as a filter, molecular sieves, resins, hollow fibers, and spiral cartridge exclusions. Preferably, a 0.2 micron aseptic filter is used.

Preferably, the liquid medium is mammalian serum, more preferably human serum, which has been filter sterilized, and which also contains carbohydrates, and antimicrobial agents. For a description of such a modified human serum, see U.S. Pat. No. 5,556,788.

EXAMPLES

Example 1

Modification of cTnI from Natural Sources

Whole molecule native cTnI was isolated from heart muscle as a single subunit and substantially purified. Under mild purification conditions, native cTnIC and cTnICT subunit complexes was also extracted from human heart tissue. The individual native cTnI subunits, as well as native complexes of cTnIC and cTnICT, were conjugated to PEG to enhance epitopic stability in a human serum derived medium as described in Examples 4 and 5.

Example 2

Modification of cTnI from Recombinant Sources

Recombinant cTnI derived from bacterial cell culture was purified from cell paste. Full-length (226 amino acid) and cleaved (153 amino acid) recombinant cTnI fragments were conjugated to PEG to enhance epitopic stability in a human serum derived medium. Additionally, full-length (226) and cleaved (153) fragments were covalently complexed TnC (from natural or recombinant sources) to yield cTnIC as described in Example 3. These complexes were conjugated to PEG as described in Example 4.

Example 3
Preparation of cTnIC Using Cleaved Recombinant cTnI

The water insoluble fraction of the recombinant cTnI cell paste was suspended in solubilization buffer (10 mM Tris-HCl, 100 mM $Na_2HPO_4$, 6M Guanidine-HCl pH 8.0) to extract the cTnI. Histidine-tagged 226 amino acid cTnI was purified using a nickel-sepharose column on an HPLC system using a stepwise pH gradient elution to recover the bound cTnI. Purified 226 amino acid cTnI was incubated with DTT to break the disulfide bridges, then incubated with iodoacetamide to block disulfide reformation. The solution was dialyzed into a 25% acetic acid solution to quench iodoacetamide activity, freeze dried using a speed vac centrifuge, and reconstituted into a 70% formic acid solution. CNBr cleavage was performed to yield the 153 amino acid cTnI fragment. The solution containing 153 amino acid cTnI was dialyzed unto PTU buffer (10 mM Tris-HCl, 100 mM $Na_2HPO_4$, 8M Urea pH 8.0) for a buffer exchange and to remove the smaller cleaved fragments. Micro BCA assays (Pierce Chemical Co., Rockford, Ill.) and Stratus CS assays were used to quantitate 153 amino acid cTnI concentration and SDS PAGE was used to evaluate the CNBr cleavage reaction. TnC was activated using NHS and EDAC then complexed to 153 amino acid cTnI to yield cTnIC. The cTnIC complex was conjugated to PEG to enhance epitopic stability in a human serum derived matrix as described in Example 4.

Example 4
Conjugation of cTnIC Complex to PEG

The cTnIC reaction mixture was diluted with chilled conjugation buffer (0.1 M phosphate pH 7.5) to a concentration of 0.1 mg/mL by the Micro BCA protein assay. The activated polymer solution was prepared by dissolving 50 mg of methoxypolyethylene glycol p-nitrophenyl carbonate (mPEG-NPC, avg. MW=5000 Da) in 1 mL of chilled conjugation buffer. 2 mL of the activated polymer solution was added to 1 mL of the diluted cTnIC solution (7700-fold PEG molar excess). The solution was gently mixed at room temperature for 2 hours, then placed at 4° C. to mix for an additional 18 hours. The PEG-cTnIC conjugate solution formed was then frozen and stored at −20° C. until use.

Example 5
Conjugation of cTnI to PEG

Lyophilized cTnI powder was reconstituted and diluted with chilled conjugation buffer (0.1 M phosphate pH 7.5) to a concentration of 0.2 mg/mL by the Micro BCA protein assay. The activated polymer solution was prepared by dissolving 50 mg of methoxypolyethylene glycol p-nitrophenyl carbonate (mPEG-NPC, avg. MW=5000 Da) in 1 mL of chilled conjugation buffer. 2 mL of the activated polymer solution was added to 1 mL of the diluted cTnI solution (2400-fold PEG molar excess). The solution was gently mixed at room temperature for 2 hours, then placed at 4° C. to mix for an additional 18 hours. The PEG-cTnIC conjugate solution formed was then frozen and stored at −20° C. until use.

Example 6
Stability of cTnIC-PEG Conjugate

The stability of the cleaved recombinant 153-amino acid cTnIC-PEG conjugate prepared according to Examples 3 and 4 was compared to that of the corresponding unconjugated proteins. Both the conjugated and unconjugated preparations were diluted in a liquid medium of human serum, and stored at −20, 4, 25, and 37° C. Initially (day 0), and after 5, 10, and 30 days, samples were removed and analyzed. The amount of cTnIC was quantified using the Dade Dimension RXL™ System. Table 1 shows the stability of unconjugated cTnIC, cTnIC conjugated with 770×PEG, and cTnIC conjugated with 7700×PEG. The results are reported as the percentage of the amount of protein detected in samples stored at 4, 25, and 37° C. relative to the amount of protein detected in samples stored at −20° C. Table 1 shows that the addition of PEG stabilizes the protein complexes at temperatures ranging from 4 to 37° C., and the effects of PEG are more pronounced when the complexes are stored at higher temperatures. Additionally, PEG added in 770- and 7700-fold molar excess is stabilizing, and the effect of PEG is more pronounced at 7700-fold molar excess.

TABLE 1

Stability of cTnIC-PEG Conjugates

| Condition | Days Stored | 4° C. | 25° C. | 37° C. |
|---|---|---|---|---|
| Unmodified cTnIC (no PEG) | 5 | 93% | 78% | 68% |
| | 10 | 80% | 62% | 51% |
| | 30 | 68% | 58% | 47% |
| cTnIC-PEG (770X PEG) | 5 | 98% | 82% | 76% |
| | 10 | 92% | 80% | 74% |
| | 30 | 89% | 69% | 60% |
| cTnIC-PEG (7700X PEG) | 5 | 97% | 95% | 95% |
| | 10 | 99% | 100% | 105% |
| | 30 | 101% | 97% | 91% |

Example 7
Stability of cTnI-PEG Conjugate

The stability of the native full length 226-amino acid cTnI-PEG conjugate prepared according to Example 5 was compared to that of the corresponding unconjugated protein. Both the conjugated and unconjugated preparations were diluted in a liquid medium of human serum, and stored at −20, 4, 25, and 37° C. Initially (day 0), and after 5, 10, and 30 days, samples were removed and analyzed. The amount of cTnI was quantified using the Dade Dimension RXL™ System. Table 2 shows the stability of unconjugated cTnI, cTnI conjugated with 200×PEG, and cTnI conjugated with 2400×PEG. The results are reported as the percentage of the amount of protein detected in samples stored at 4, 25, and 37° C. relative to the amount of protein detected in samples stored at −20° C. Table 2 shows that the addition of PEG stabilizes the protein complexes at temperatures ranging from 4 to 37° C. Additionally, PEG added in 200- and 2400-fold molar excess is stabilizing, and the effect of PEG is more pronounced at 2400-fold molar excess.

TABLE 2

Stability of cTnI-PEG Conjugates

| Condition | Days Stored | 4° C. | 25° C. | 37° C. |
|---|---|---|---|---|
| Unmodified cTnI (no PEG) | 5 | 66% | 35% | 11% |
| | 10 | 65% | 26% | 7% |
| cTnI-PEG (200X PEG) | 5 | 74% | 47% | 23% |
| | 10 | 65% | 33% | 23% |
| cTnI-PEG (2400X PEG) | 5 | 102% | 100% | 110% |
| | 10 | 98% | 98% | 106% |
| | 30 | 94% | 108% | 81% |

Modifications of the above-described modes for carrying out the invention that are obvious to persons of skill in the field of protein chemistry are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of stabilizing a subunit complex of a multi-subunit protein complex, wherein the subunit complex is cardiac troponin IC (cTnIC), comprising mixing a solution of cTnIC with an active polymer to form a stabilized cTnIC-polymer conjugate.

2. The method according to claim 1, wherein the subunit complex is a fragment of cTnIC that is capable of being recognized by an antibody specific for at least one subunit selected from the group consisting of cTnI, cTnC, and cTnIC.

3. The method according to claim 1, wherein the polymer has an average molecular weight ranging from about 100 to about 200,000 daltons.

4. The method according to claim 1, wherein the polymer has an average molecular weight ranging from about 1000 to about 40,000 daltons.

5. The method according to claim 1, wherein the polymer has an average molecular weight ranging from about 2500 to about 10,000 daltons.

6. The method according to claim 1, wherein the active polymer is conjugated with the cTnIC in a molar ratio ranging from about 1:1 to about 20,000:1.

7. The method according to claim 1, wherein the active polymer is conjugated with the cTnIC in a molar ratio ranging from about 770:1 to about 11,550:1.

8. The method according to claim 1, wherein the active polymer is conjugated with the cTnIC in a molar ratio ranging from about 6000:1 to about 8000:1.

9. The method according to claim 1, wherein th e polymer is a synthetic polymer.

10. The method according to claim 9, wherein the synthetic polymer is selected from the group consisting of polyalkylene glycols, polyoxyethylated polyols, polyvinylpyrrolidone, polyhydroxyethyl methacrylate, polyvinyl alcohols, polyurethane, and derivatives thereof.

11. The method according to claim 9, wherein the synthetic polymer is polyethylene glycol (PEG) or a derivative thereof capable of being covalently bound to a protein.

12. The method according to claim 11, wherein the PEG has an average molecular weight ranging from about 2500 to about 10,000 daltons.

13. The method according to claim 11, wherein the PEG has an average molecular weight ranging from about 5000 to 7000 daltons.

14. The method according to claim 11, wherein the PEG is conjugated with the cTnIC in a molar ratio ranging from about 1:1 to about 20,000:1.

15. The method according to claim 11, wherein the PEG is conjugated with the cTnIC in a molar ratio ranging from about 770:1 to about 11,550:1.

16. The method according to claim 11, wherein the PEG is conjugated with the cTnIC in a molar ratio ranging from about 6000:1 to about 8000:1.

17. The method according to claim 11, wherein the PEG is monomethoxy-PEG p-nitrophenyl carbonate.

18. The method according to claim 1, wherein the multisubunit protein complex is in a liquid medium.

* * * * *